United States Patent [19]

Ergan et al.

[11] Patent Number: 5,010,006

[45] Date of Patent: Apr. 23, 1991

[54] LIPASE IMMDOILIZED BY CROSS-LINKING WITH INERT PROTEIN FOR GLYCERIDE SYNTHESIS

[75] Inventors: Francoise Ergan; Michael Trani, both of Montreal; Gërald Andre, Ile Bizard, all of Canada

[73] Assignee: Her Majesty the Queen in Right of Canada as represented by the National Research Council of Canada, Ottawa, Canada

[21] Appl. No.: 231,221

[22] Filed: Aug. 11, 1988

[51] Int. Cl.$^5$ .................... C12N 11/02; C12N 11/00; C12P 7/64

[52] U.S. Cl. .................... 435/177; 435/134; 435/174

[58] Field of Search ............... 435/134, 174, 177, 181, 435/198

[56] References Cited

U.S. PATENT DOCUMENTS

| | | | |
|---|---|---|---|
| 3,705,084 | 12/1972 | Reynolds | 435/180 |
| 3,796,634 | 3/1974 | Haynes et al. | 435/176 |
| 4,464,468 | 8/1984 | Arrameas et al. | 435/179 X |
| 4,472,503 | 9/1984 | Matsuo et al. | 435/180 X |
| 4,798,793 | 1/1989 | Eigtred | 435/198 X |

OTHER PUBLICATIONS

G. Broun et al., "New Methods for Binding Enzyme Molecules into a Water-Insoluble Matrix: Properties after Insolubilization", Biotechnology and Bioengineering, vol. XV, pp. 359–375 (1973).

*Primary Examiner*—David M. Naff
*Attorney, Agent, or Firm*—Oblon, Spivak, McClelland, Maier & Neustadt

[57] ABSTRACT

A dry porous macromolecular matrix is prepared comprising a cross-linked mixture of 69.9 to 86.6% by weight of an inert protein 0.4 to 10.2% by weight of a lipase enzyme and about 11.7 to 23% by weight of a cross-linking agent. The matrix is prepared by reacting the lipase, inert protein and cross-linking agent in a buffer solution, freezing the resulting reacted mixture at a temperature ranging between $-20°$ C. and $-195°$ C., allowing the frozen mixture to thaw to a temperature ranging from $4°$ C. to $25°$ C., and rinsing and drying the resulting product at room temperature.

16 Claims, 21 Drawing Sheets

LIPASE IMMDOILIZED BY CROSS-LINKING WITH INERT PROTEIN FOR GLYCERIDE SYNTHESIS

FIELD OF THE INVENTION

The present invention relates to a dry porous macromolecular matrix comprising a cross-linked mixture of an inert protein, a lipase enzyme and a cross-linking agent. This matrix is particularly suitable or adapted to catalyze the reaction of fatty acids such as oleic acid and glycerol to produce mono-, di- and tri-olein.

BACKGROUND OF THE INVENTION

The use of immobilized lipase preparations for the transesterification of fats is well known. For example, in UK Patent 1,577,933, an immobilized lipase suitable for transesterification is attached on an indifferent particulate carrier which may be diatomaceous earth or alumina and which exhibits a very high surface area. It has also been proposed to prepare an immobilized lipase preparation for interesterification with n-hexane as a solvent comprising lipase and a strong anion exchange resin (see European Journal of Applied Microbiology and Biotechnology, no. 14, p. 1–5 (1982)). E.P.O. application No. 0069599 discloses a lipase enzyme suported on a carrier such as Celite ® for continuous interesterification in a column.

In Biotechnology and Bioengineering, vol. XV, p. 359–375, 1973, G. Broun et al, methods of cross-linking enzyme molecules inside a matrix with or without an inactive protein are described. More specifically, the method comprises the cross-linking of an enzyme molecule with an inactive protein, such as albumin, in the presence of a bifunctional cross-linking agent without any preformed matrix.

In practice, this article teaches the mixing of albumin, glutaraldehyde and an enzyme in a phosphate buffer, freezing the solution obtained at −30° C. and allowing the frozen mass to warm at 4° C. After standing for 4 hours at 4° C., the spongelike proteinic copolymer is thoroughly rinsed, lyophilized and ground. It is then suitable for suspending in a mixed solution of substrate or for pouring into a column with a flux of substrate solution flowing through it. Examples using glucose oxidase, urease, trypsin and catalase are given.

Unfortunately, it has been found that when any of the enzymes used in the G. Broun et al disclosure is replaced by lipase, there is no obtention of a solid matrix. It is however possible to obtain the desired porous matrix by increasing the amount of bifunctional cross-linking agent but in this situation, the lipase enzyme loses its activity after lyophilization.

Therefore, a method making the use of active immobilized lipase possible would be highly desirable.

SUMMARY OF THE INVENTION

In accordance with the present invention, there is provided a dry porous macromolecular matrix which comprises a cross-linked mixture of 69.9% to 86.6% by weight of an inert protein, 0.4% to 10.2% by weight of a lipase enzyme and a cross-linking agent, the amount of cross-linking agent being from about 11.7% to 23% by weight.

Also in accordance with the present invention, there is provided an improvement in the process for preparing the dry porous macromolecular matrix of the present invention whereby a reaction mixture of the lipase enzyme, inert protein, cross-linking agent and buffer is frozen at a temperature ranging from −20° C. to −195° C. and allowed to thaw in distilled water at a temperature ranging from 4° C. to 25° C. after which the matrix is rinsed with water and acetone. The matrix is then vigorously wrung and dried at room temperature for a period of about 12 hours. The matrix of the present invention may be used for the catalysis of fatty acids such as oleic acid with glycerol into compounds such as mono-, di- and tri-olein.

IN THE DRAWINGS

DETAILED DESCRIPTION OF THE INVENTION

The Macromolecular Matrix

Figure 1:
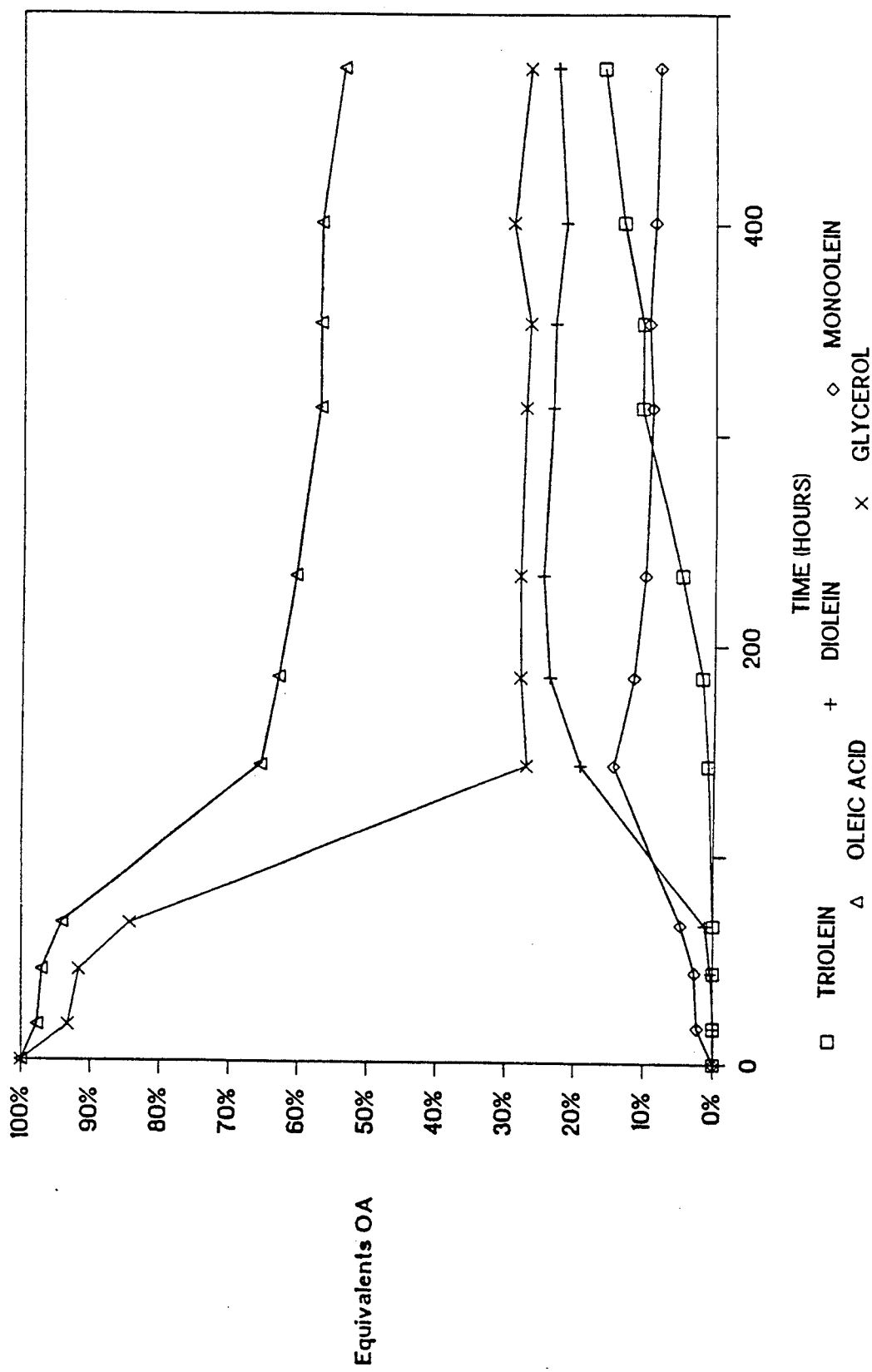
FIG. 1 represents the consumption of oleic acid through its enzymatic reaction with lipase and glycerol and the corresponding appearance of reaction products when concentrated lipase obtained from *Rhizopus arrhizus* and immobilized using glutaraldehyde at a concentration of 1.125% is used.
Figure 2:
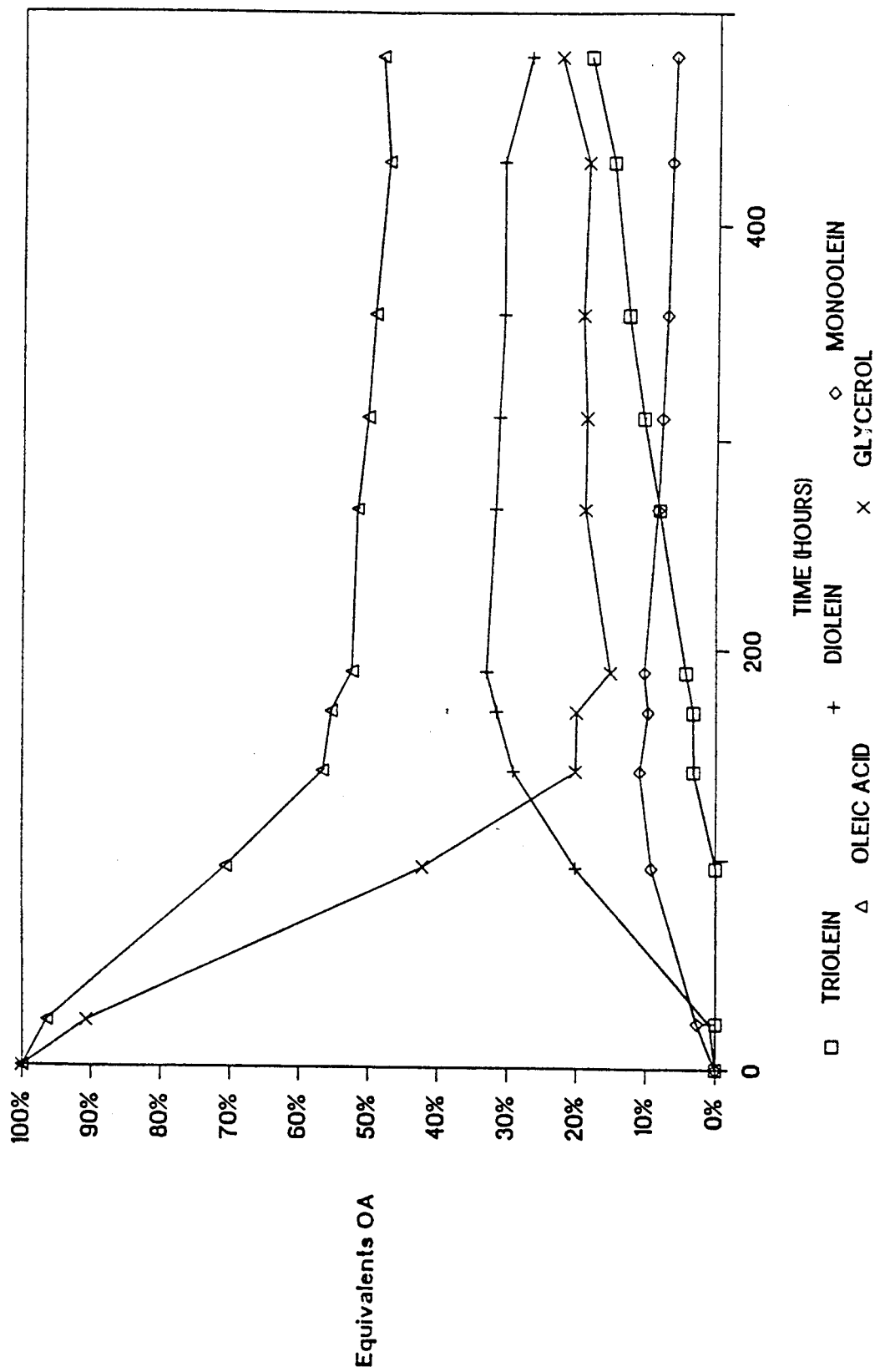
FIGS. 2 to 5 represent successive cycles of consumption of oleic acid through its enzymatic reaction with lipase and glycerol and the corresponding appearance of reaction products when immobilized concentrated lipase obtained from *Rhizopus arrhizus* is reused.
Figure 3:
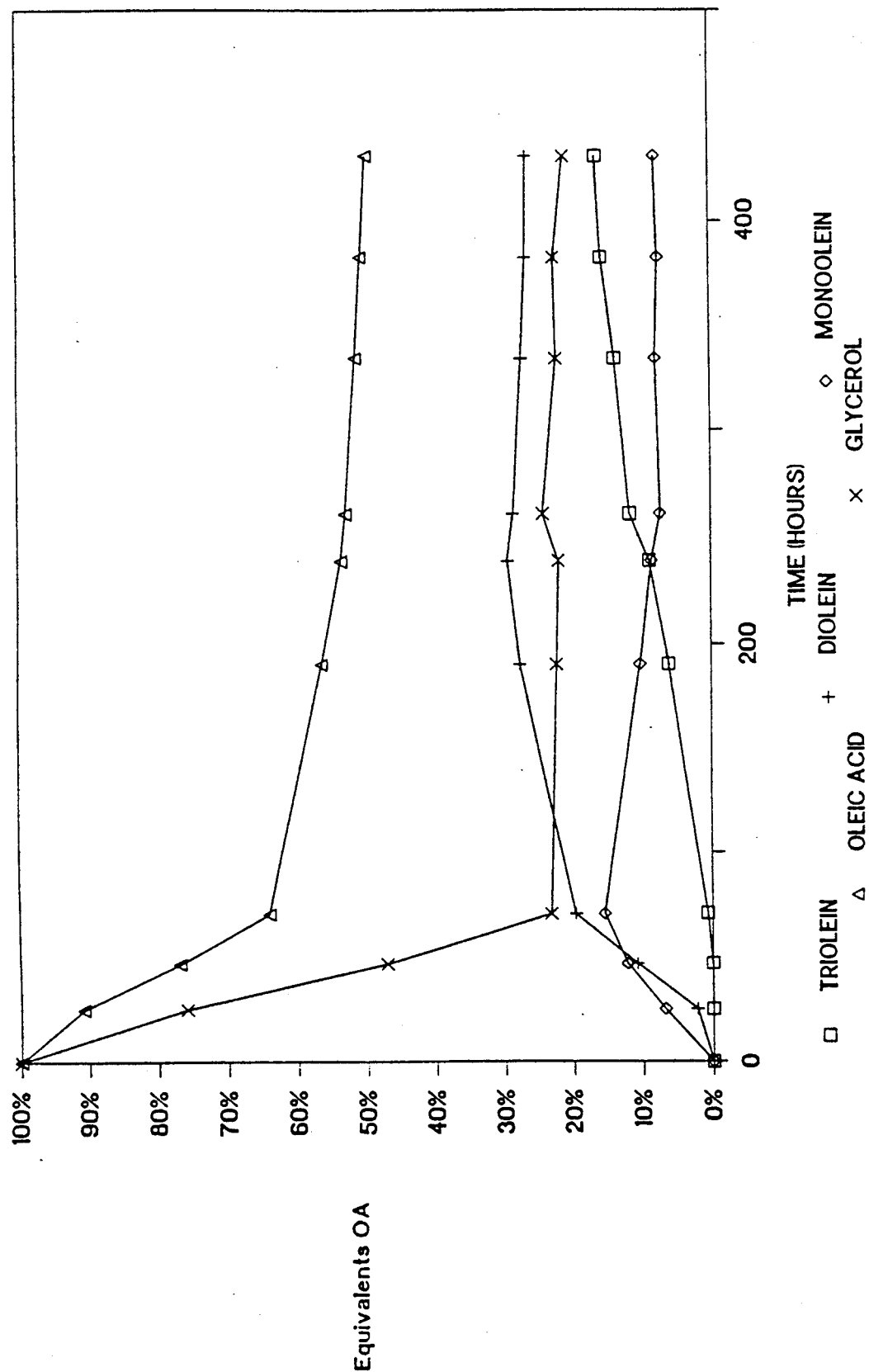
Figure 4:
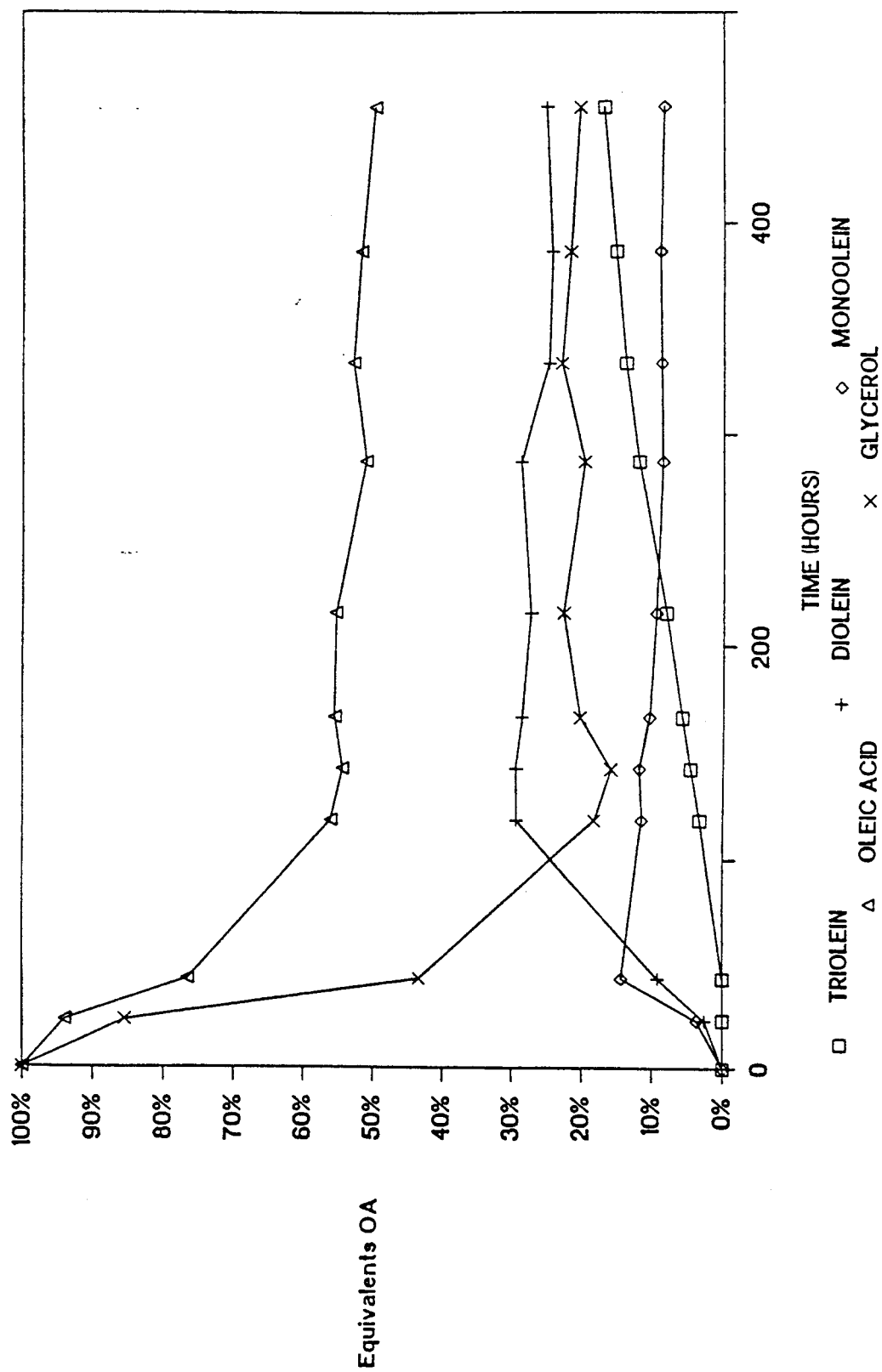
Figure 5:
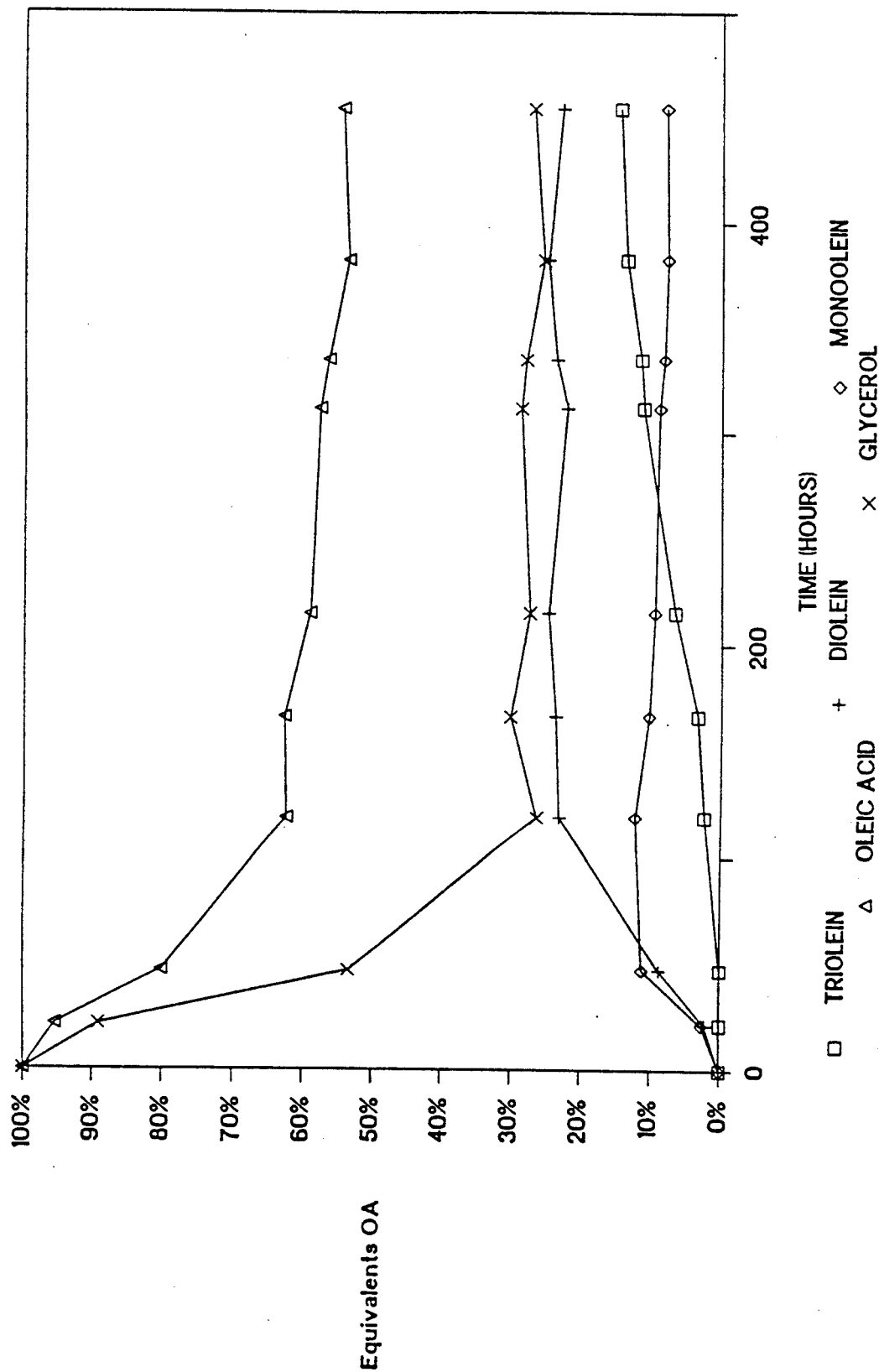

The dry porous macromolecular matrix of the present invention is a cross-linked mixture of an inert carrier, a lipase enzyme and a cross-linking agent, preferably a bifunctional cross-linking agent. More specifically, the matrix contains from 69.9% to 86.6% of inert protein, 0.4% to 10.2% by weight of lipase enzyme and 11.7 to 23% by weight of cross-linking agent. The matrix can be used as such in esterification procedures or can be ground to a fine powder.

The Inert Carrier

The inert support is used as an enzyme carrier. It may be in the form of powder, fibers or the like although it is preferable that the carrier be in the form of granules in view of the continuous use of the resulting enzyme preparation. It is usually preferred to use inert proteins which are, in the context of the present invention, very suitable inert supports.

As inert protein, human and animal albumin may be used, for example, bovine albumin, fibrinogen, hemoglobin and the like. The amount of inert protein in the initial mixture is 5% by weight. In the final macromolecular matrix, the quantity of inert protein may range from 69.9% to 86.6% by weight.

The Enzyme

The lipase enzyme used for immobilization purposes in accordance with the present invention may be selected from lipases originating from *Candida cylindracea*, *Mucor miehei*, *Rhizopus arrhizus*, *Rhizopus delemar* and the like. These enzymes are bonded to an inert protein carrier through a cross-linking agent. The mixture ratios of the enzyme to the carrier may vary from 6.3:1200 to 157.1:1200.

The Cross-Link Agent

The cross-linking agent is used to bound the enzyme onto the inert carrier. Although it is possible to employ various types of cross-linking agents, it has been found that glutaraldehyde in quantities ranging between 11.7% and 23% by weight is preferred.

The Process

In order to disperse, adsorb or bond the enzyme or the enzyme-containing material in or to the carrier, for example, the enzyme or the enzyme-containing material is dissolved in a buffer solution and the resulting solution is admixed with the carrier.

Thus, in a buffered solution, there is added 5% by weight of an inert carrier, preferably an inert protein, 0.75% to 1.5% by weight of a cross-linking agent and 50 to 440 $\mu$l of lipase enzyme diluted in the buffer.

After allowing the mixture to stand at room temperature for a period of from 5 to 10 minutes to allow prereticulation or cross-linking between the inert carrier and the enzyme via the cross-linking agent, the mixture is then frozen at a temperature ranging from $-20°$ C. to $-195°$ C. until ready to use. When the matrix is to be used in a catalytic reaction, the frozen mixture is thawed slowly up to a temperature that may vary from 4° C. to 25° C. in distilled water, thereby yielding a solid matrix. After thorough washing with water to remove any unreacted compound and any free enzyme, the matrix is blotted dry on filter paper and shaked in acetone for about two hours to eliminate any water in the core of the matrix. The matrix is then allowed to dry on filter paper at room temperature for a period of 3 to 24 hours. Preferably, the reaction mixture is to be frozen at $-80°$ C., thawed at 4° C. and allowed to dry for 12 hours. It is to be noted that the drying step is essential to the process of the present invention since the presence of water prevents the catalytic reaction of fatty acids with glycerol. The final product obtained is a porous macromolecular matrix.

Reaction Substrates

Typical examples of fatty substrate used in the context of the present invention is a mixture of fatty acids and short alcohols such as methanol, ethanol, glycerol and the like. Furthermore, the substrate may include other fatty esters on which a lipolytic enzyme can act, such as monoglycerides, diglycerides, methyl esters, ethyl esters or the like. Also fatty acids having $C_3$ to $C_{22}$ carbon atoms may be used as substrates either alone or together with these fatty esters.

The substrate should be a liquid at the reaction temperature, and no organic solvent should be used. The reaction medium is composed of only the required substrates for the reaction. Preferably, the most desirable substrate to be used in the context of the present invention is a mixture of oleic acid and glycerol in stoichiometric proportions.

Catalytic Reaction

The catalytic reaction of the present invention through which fatty acids and alcohols, such as oleic acids and glycerol, are preferably transformed into mono-, di- and tri-olein is carried out by continuously or repeatedly contacting the enzyme or the enzyme preparation with a supply of the fatty acids and glycerol.

The enzymatic reaction of the present invention can be carried out in a batchwise operation or in a continuous operation using for example a fluidized bed of the enzyme preparation or a column packed with the enzyme preparation.

Generally, a mixture containing between 0.5 to 10 g of oleic acid and between 0.0543 to 1.086 g of glycerol and from 50 to 440 $\mu$l of lipase immobilized in the previously described matrix is strongly agitated at a temperature ranging between 25° C. and 60° C. for a time ranging from 10 to 1000 hours. From time to time, samples of the reaction mixture are analyzed in order to measure the amount of substrate still in solution and to analyze the various reaction products.

With the immobilization technique of the present invention, it is possible to use the immobilized enzyme for up to four successive cycles before observing a decline in enzymatic activity.

The following examples are disclosed in order to illustrate rather than limit the scope of the present invention.

EXAMPLE 1

Immobilization of Lipase Originating From *Rhizopus arrhizus* Onto Bovine Albumin 50 µl (222 units, 0.63 mg protein) of a commercially available concentrated lipase originated from *Rhizopus arrhizus* (Sigma no. L—4384) was diluted in 390 µl of phosphate buffer, 0.02 M, pH 6.72. To the resulting solution was added 1 ml of phosphate buffer 0.02 M, pH 6.72, 0.6 ml of bovine albumin 20% and 0.36 ml of glutaraldehyde 7.5%. The final mixture demonstrated a final albumin concentration of 5% and a final glutaraldehyde concentration of 1.125% with a final volume of 2.4 ml. The mixture is then allowed to stand at room temperature for 10 minutes in order to permit prereticulation or crosslinking between the albumin and the lipase via glutaraldehyde. The resulting mixture is then frozen at −80° C. When it is desired to use the enzyme bound macromolecular matrix, the mixture is slowly thawed up to a temperature of 4° C. in distilled water. The resulting matrix is then thoroughly rinsed, vigorously wrung out, washed with acetone and dried on filter paper at room temperature for 12 hours. The final matrix demonstrated a final albumin concentration of 81.3% and a final glutaraldehyde concentration 18.3%.

EXAMPLE 2

The procedure described in Example 1 was repeated in order to obtain a final glutaraldehyde concentration of 0.75% in the mixture which necessitated the use of 0.36 ml of glutaraldehyde 5% in the initial reaction mixture. After drying, the albumin concentration was 86.6% and the glutaraldehyde concentration 13%.

EXAMPLE 3

The procedure described in Example 1 was repeated in order to obtain a final glutaraldehyde concentration of 1.5% in the mixture which necessitated the use of 0.36 ml of glutaraldehyde 10% in the initial reaction mixture. After drying, the albumine concentration was 76.6% and the glutaraldehyde concentration 23%.

EXAMPLE 4

Immobilization of Lipase Originating From *Rhizopus delemar* Onto Bovine Albumin The procedure described in Example 1 was repeated using 440 µl (1571.4 units, 15.71 mg protein) of a commercially available concentrated lipase originated from *Rhizopus delemar* instead of lipase originated from *Rhizopus arrhizus*. The procedure of Example 1 was repeated in order to obtain a final glutaraldehyde concentration of 0.75% in the mixture which necessitated the use of 0.36 ml of glutaraldehyde 5% in the initial reaction mixture. After drying, the albumin concentration was 78.1% and the glutaraldehyde concentration 11.7%.

EXAMPLE 5

The procedure described in Example 4 was repeated in order to obtain a final glutaraldehyde concentration of 1.125% in the mixture which necessitated the use of 0.36 ml of glutaraldehyde 7.5% in the initial reaction mixture. After drying, the albumin concentration was 73.8% and the glutaraldehyde concentration 16.6%.

EXAMPLE 6

The procedure described in Example 4 was repeated in order to obtain a final glutaraldehyde concentration of 1.5% in the mixture, which necessitated the use of 0.36 ml of glutaraldehyde 10% in the initial reaction mixture. After drying, the albumin concentration was 69.9% and the glutaraldehyde concentration 21%.

EXAMPLE 7

Immobilization of Lipase Originating From *Candida cylindracea* Onto Bovine Albumin The procedure described in Example 1 was repeated using 440 µl (1571.4 units, 3.96 mg protein) of a commercially available concentrated lipase originated from *Candida cylindracea* instead of lipase originated from *Rhizopus arrhizus*. The procedure of Example 1 was repeated in order to obtain a final glutaraldehyde concentration of 0.75% in the mixture which necessitated the use of 0.36 ml of glutaraldehyde 5% in the initial reaction mixture. After drying, the albumin concentration was 84.5% and the glutaraldehyde concentration 12.7%.

EXAMPLE 8

The procedure described in Example 7 was repeated in order to obtain a final glutaraldehyde concentration of 1.5% in the mixture which necessitated the use of 0.36 ml of glutaraldehyde 10% in the initial reaction mixture. After drying, the albumin concentration was 75% and the glutaraldehyde concentration 22.5%.

EXAMPLE 9

The procedure described in Example 7 was repeated in order to obtain a final glutaraldehyde concentration of 1.125% in the mixture which necessitated the use of 0.36 ml of glutaraldehyde 7.5% in the initial reaction mixture. After drying, the albumin concentration was 79.5% and the glutaraldehyde concentration 17.9%.

EXAMPLE 10

Transformation of Oleic Acid Into Mono-, Di- and Tri-Olein 0.5 g of oleic acid and 0.05 g of glycerol were reacted with the support prepared in Example 1 by strongly agitating the reaction mixture on an Eppendorf® mixer at 34° C. FIGS. 1 to 5 represent the successive cycles through which oleic acid progressively reacted to yield the various reaction products. The results are expressed as the percentage of the number of moles of oleic acid present in the initial reaction medium. Between each reaction cycle, the enzymatic support was vigorously washed with acetone for 24 hours and dehydrated at room temperature using air and filter paper.

As it can be seen from FIGS. 1 to 5, a decrease in enzymatic activity is observed after the fourth reaction cycle although the enzyme is still active right up to the seventh cycle.

EXAMPLE 11

Figure 6:
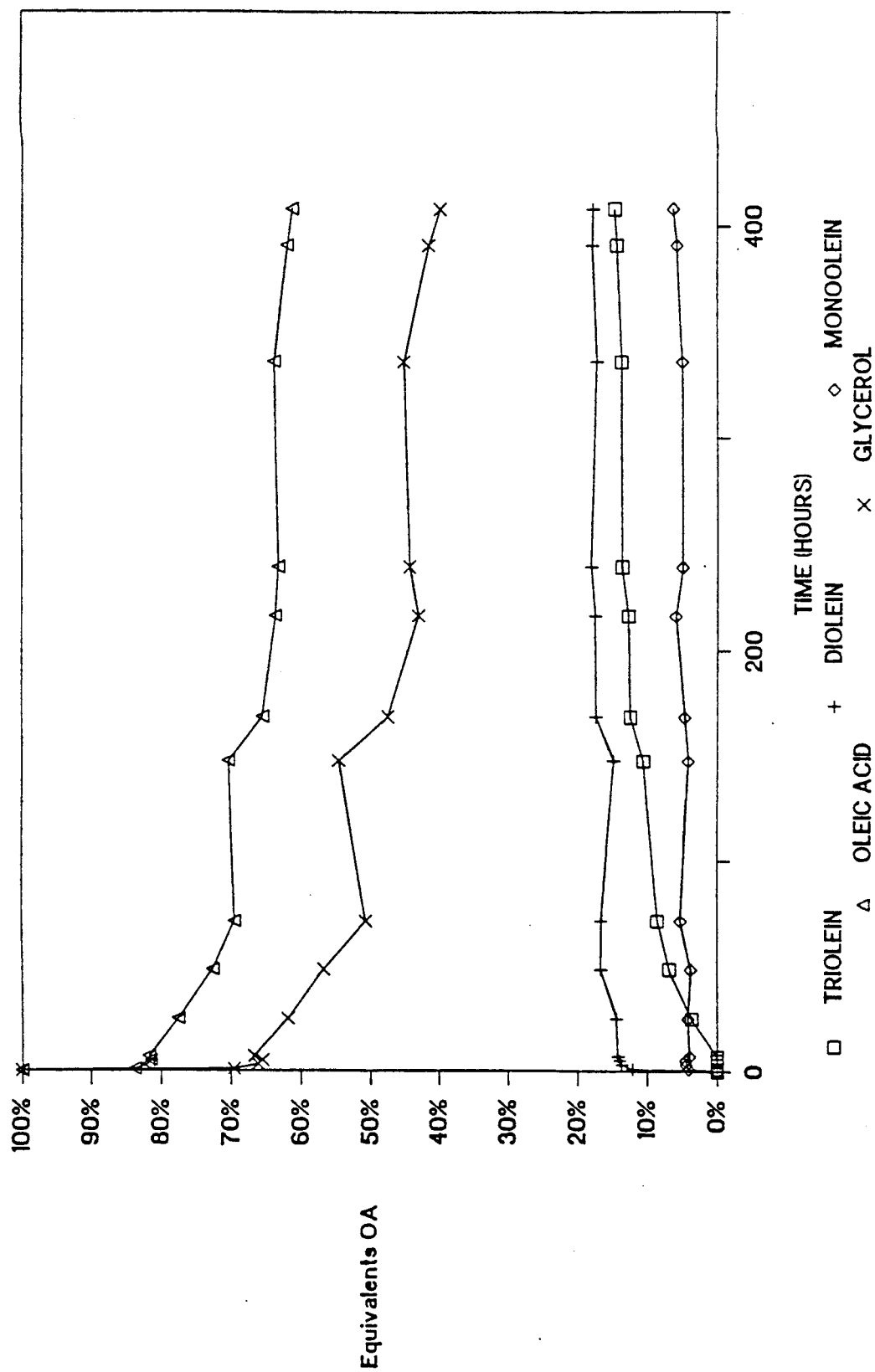
FIG. 6 represents the consumption of oleic acid through its enzymatic reaction with lipase and glycerol and the corresponding appearance of reaction products when a solution of free lipase obtained from *Rhizopus arrhizus* is used.
Figure 7:
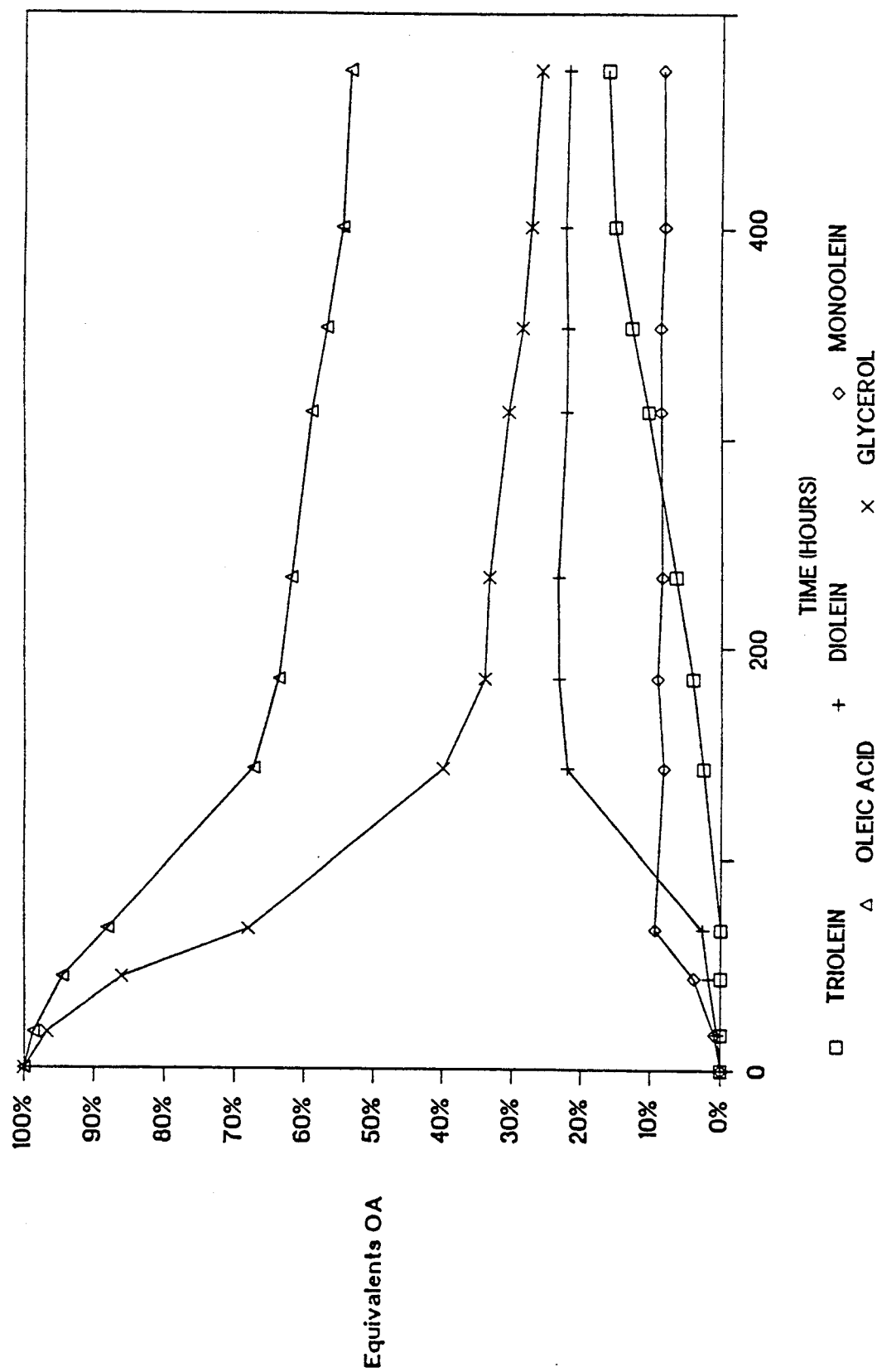
FIGS. 7 to 11 represent the first and successive cycles of consumption of oleic acid through its enzymatic reaction with lipase and glycerol and the corresponding appearance of reaction products when concentrated lipase obtained from *Rhizopus delemar* and immobilized using glutaraldehyde at a concentration of 1.125% is reused.
Figure 8:
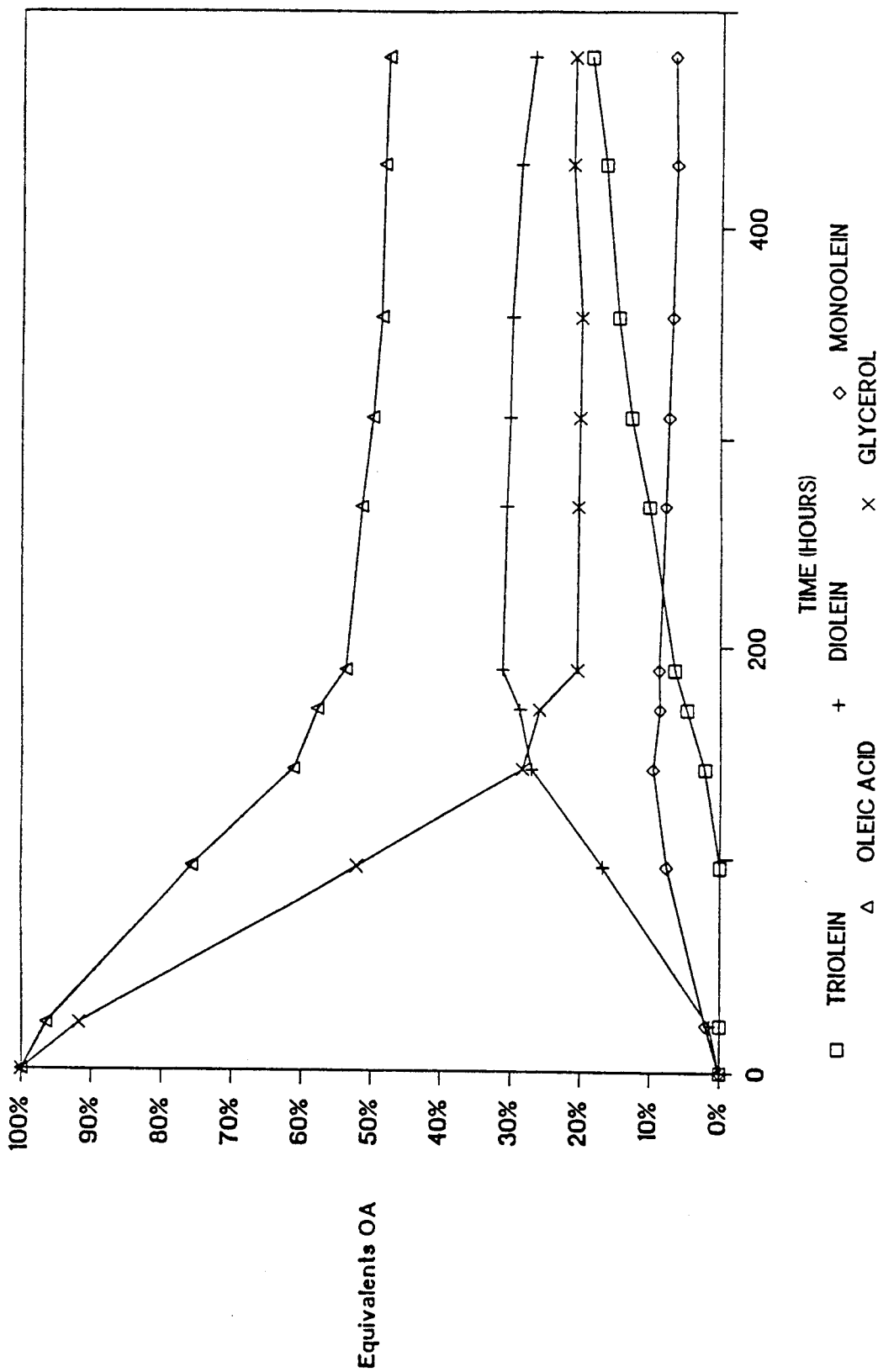
Figure 9:
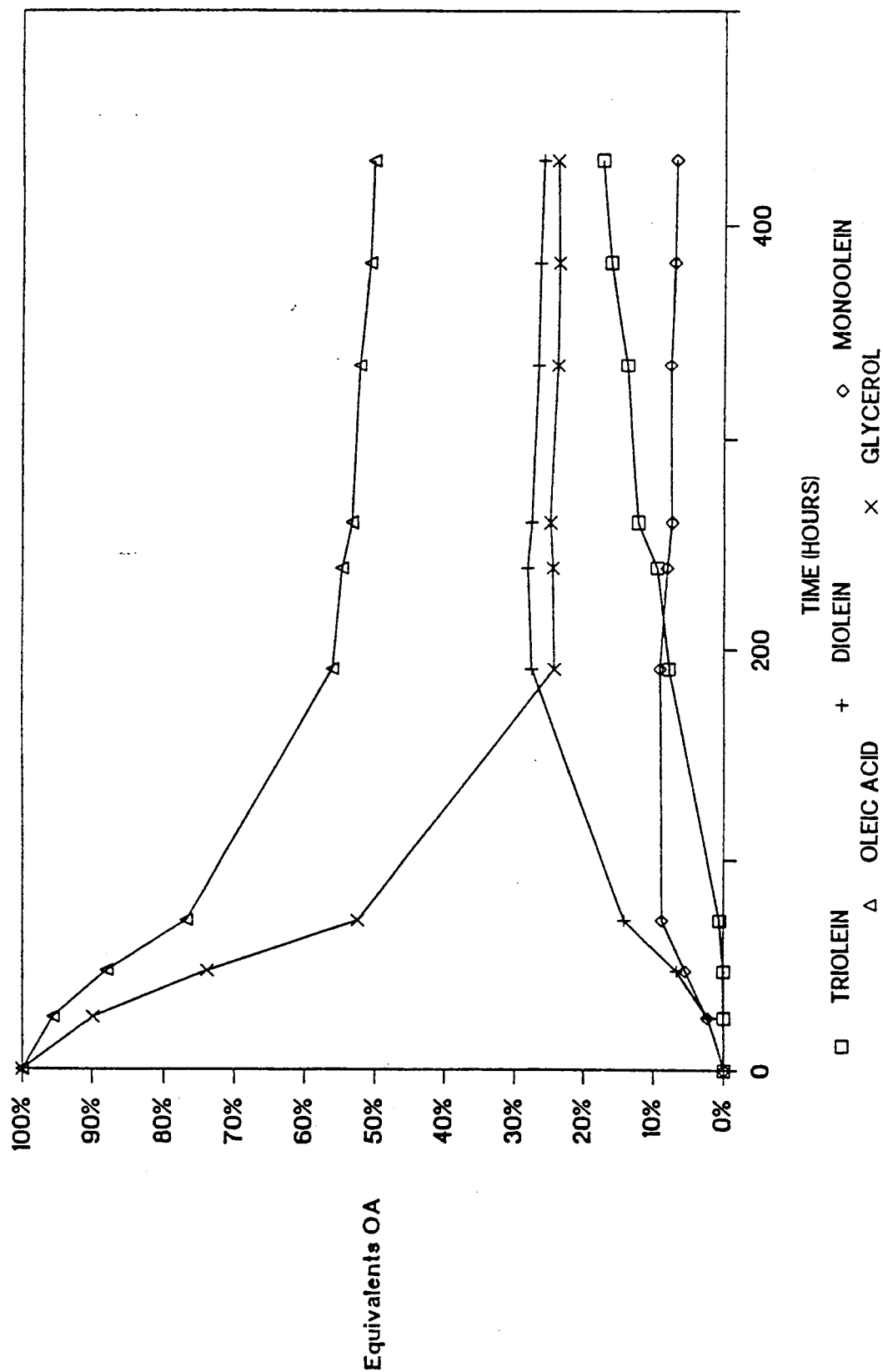
Figure 10:
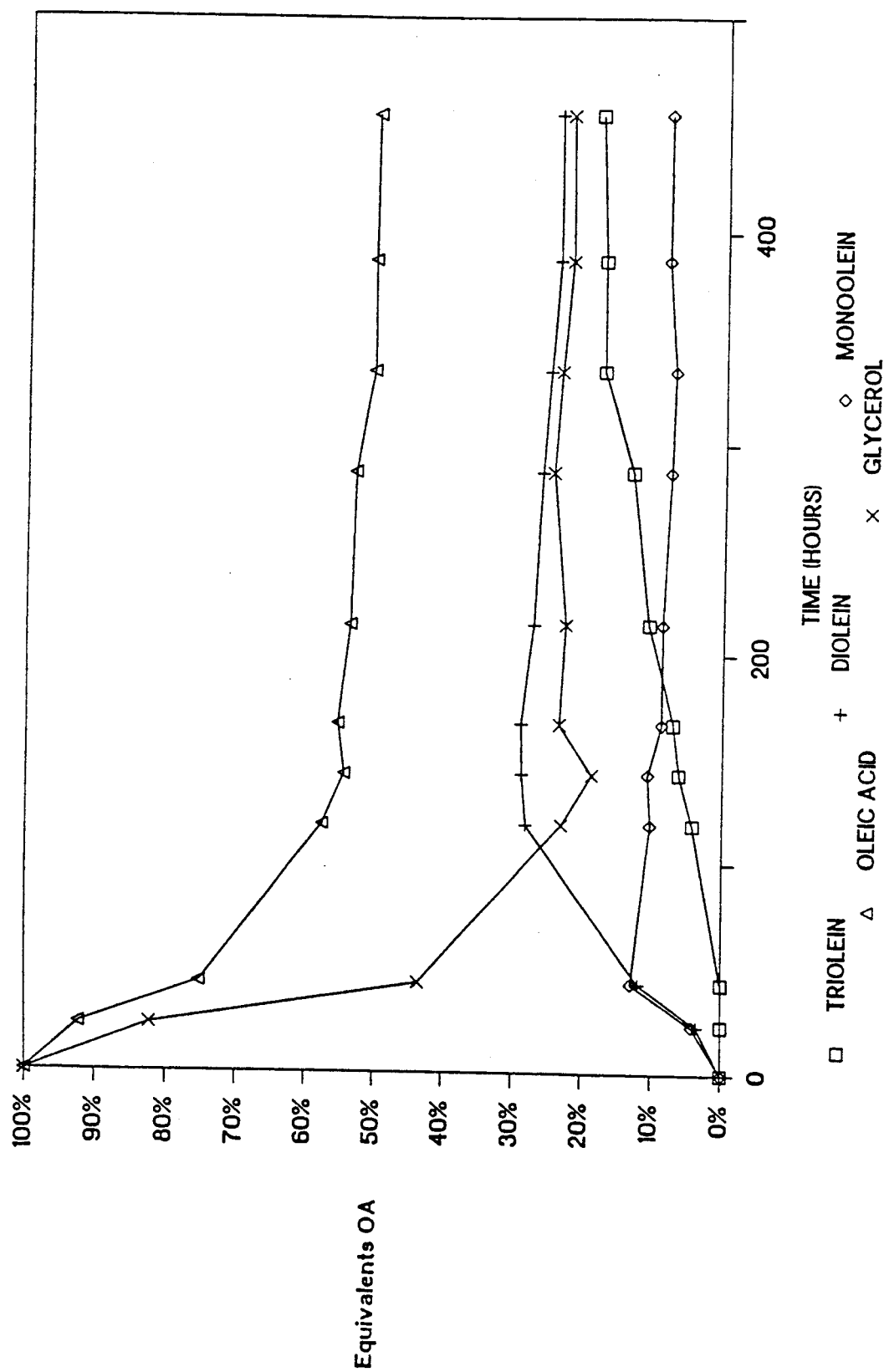
Figure 11:
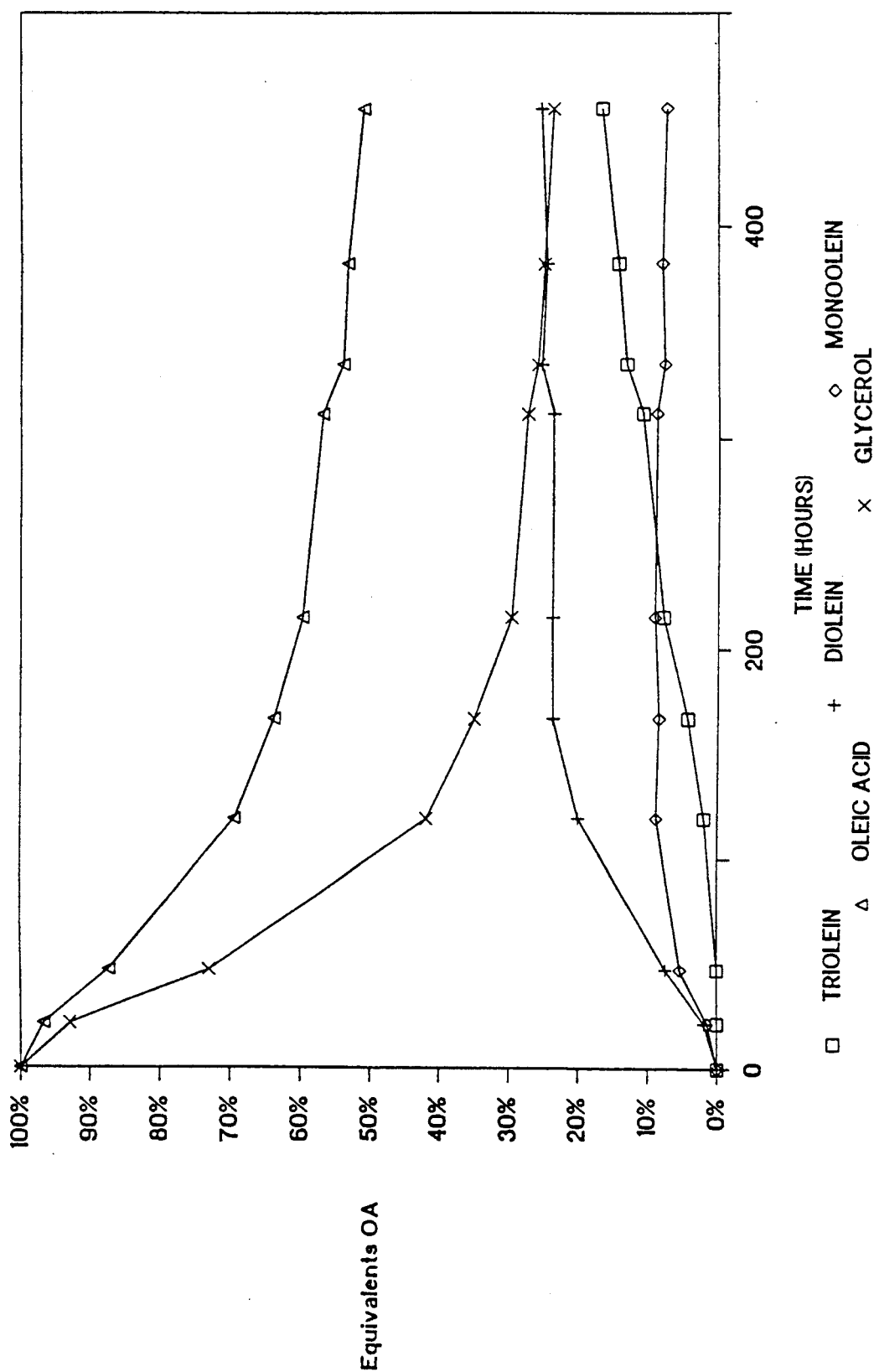

The procedure described in Example 10 was repeated but 50 μl of a solution of free lipase obtained from *Rhizopus arrhizus* were used instead of the support of Example 1. Results are shown in FIG. 6.

EXAMPLE 12

Figure 14:
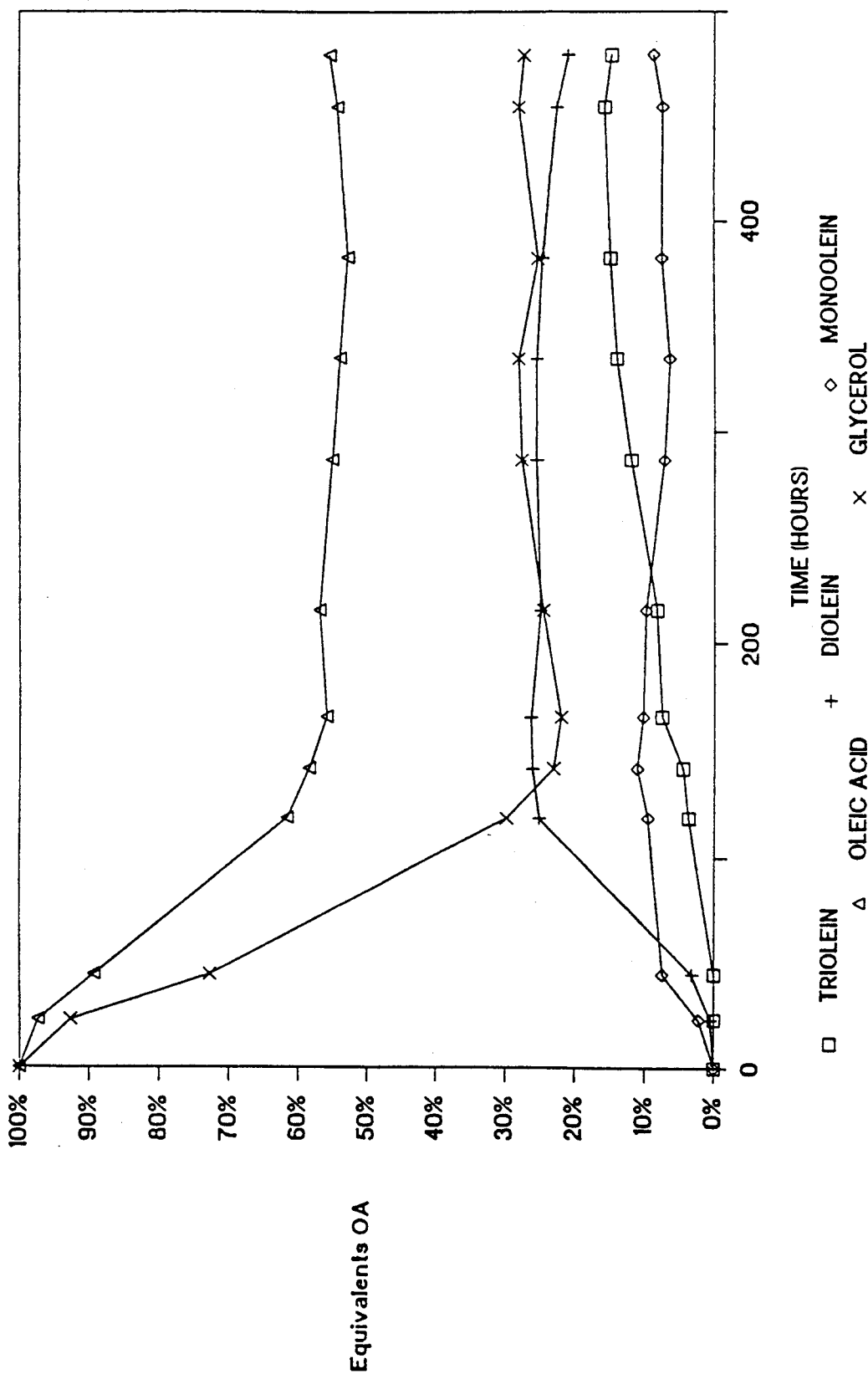
FIG. 14 represents the consumption of oleic acid through its enzymatic reaction with lipase and glycerol and the corresponding appearance of reaction products when concentrated lipase obtained from *Rhizopus arrhizus* and immobilized using glutaraldehyde at a concentration of 0.75% is used.

The procedure described in Example 10 was repeated using the support of Example 2 as the source of lipase. Results are shown in FIG. 14.

EXAMPLE 13

Figure 15:
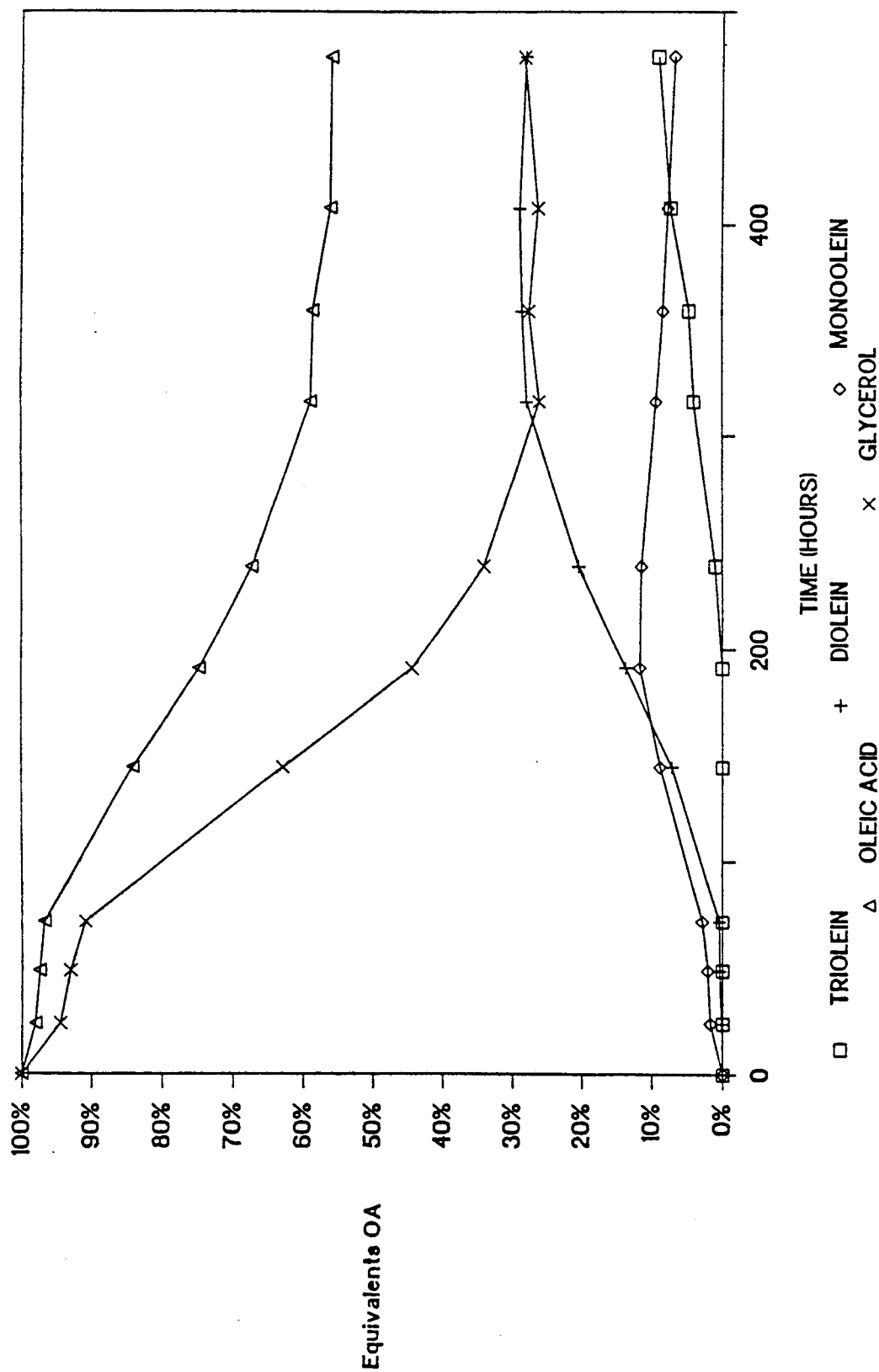
FIG. 15 represents the consumption of oleic acid through its enzymatic reaction with lipase and glycerol and the corresponding appearance of reaction products when concentrated lipase obtained from *Rhizopus arrhizus* and immobilized using glutaraldehyde at a concentration of 1.5% is used.

The procedure described in Example 10 was repeated using the support of Example 3 as the source of lipase. Results are shown in FIG. 15.

EXAMPLE 14

Figure 16:
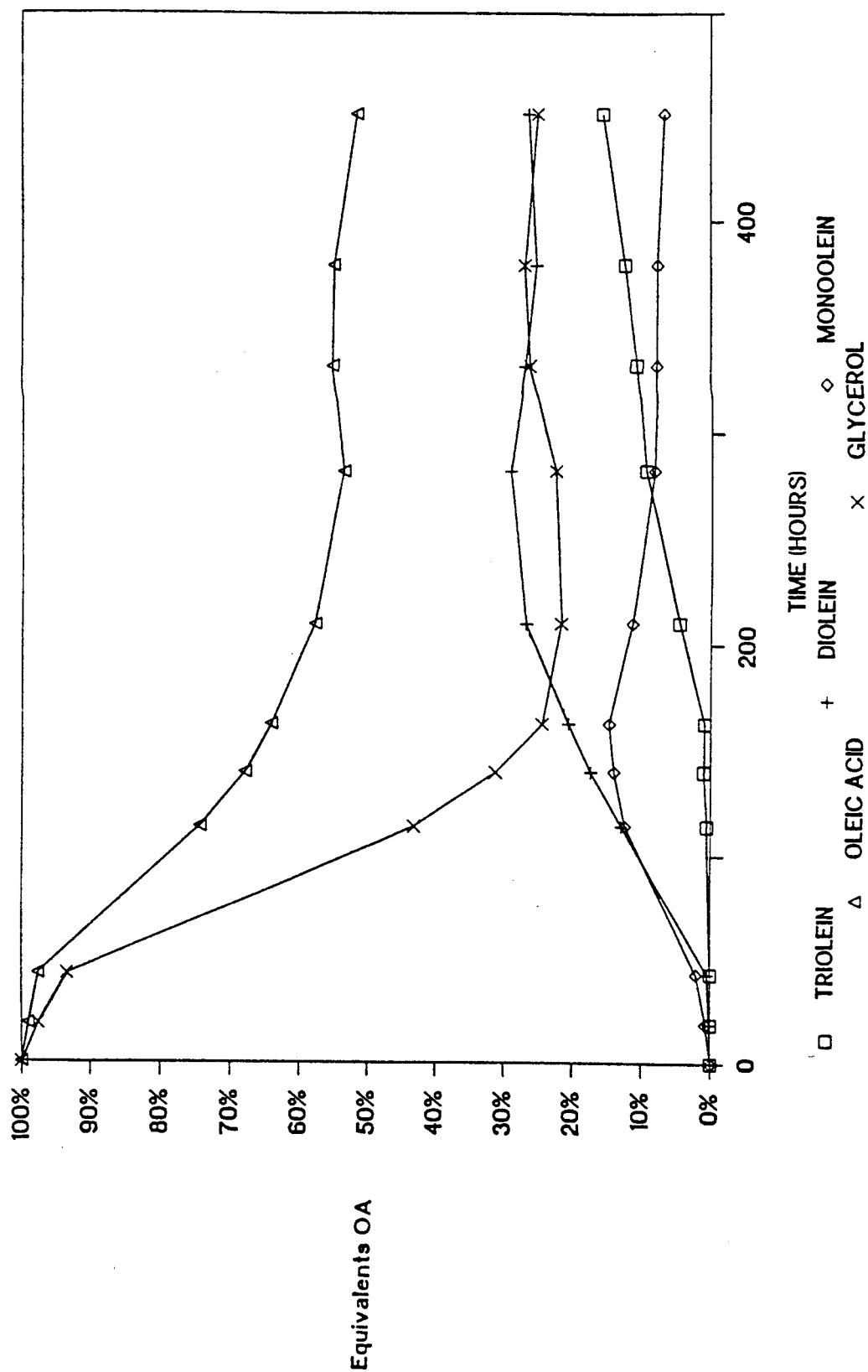
FIG. 16 represents the consumption of oleic acid through its enzymatic reaction with lipase and glycerol and the corresponding appearance of reaction products when concentrated lipase obtained from *Rhizopus delemar* and immobilized using glutaraldehyde at a concentration of 0.75% is used.

The procedure described in Example 10 was repeated using the support of Example 4 as the source of lipase. Results are shown in FIG. 16.

EXAMPLE 15

Figure 17:
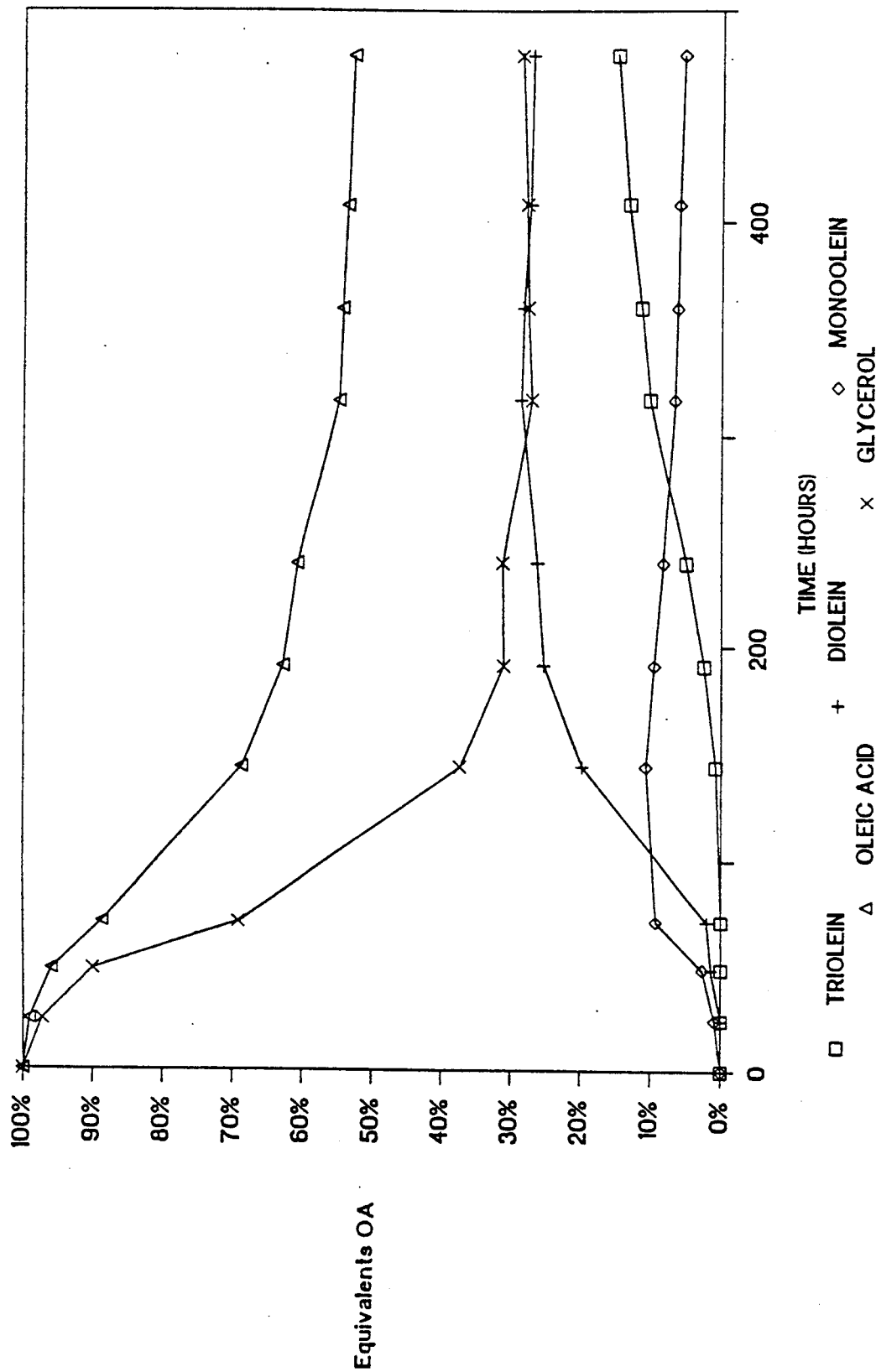
FIG. 17 represents the consumption of oleic acid through its enzymatic reaction with lipase and glycerol and the corresponding appearance of reaction products when concentrated lipase obtained from *Rhizopus delemar* and immobilized using glutaraldehyde at a concentration of 1.5% is used.

The procedure described in Example 10 was repeated using the support of Example 6 as the source of lipase. Results are shown in FIG. 17.

EXAMPLE 16

Figure 18:
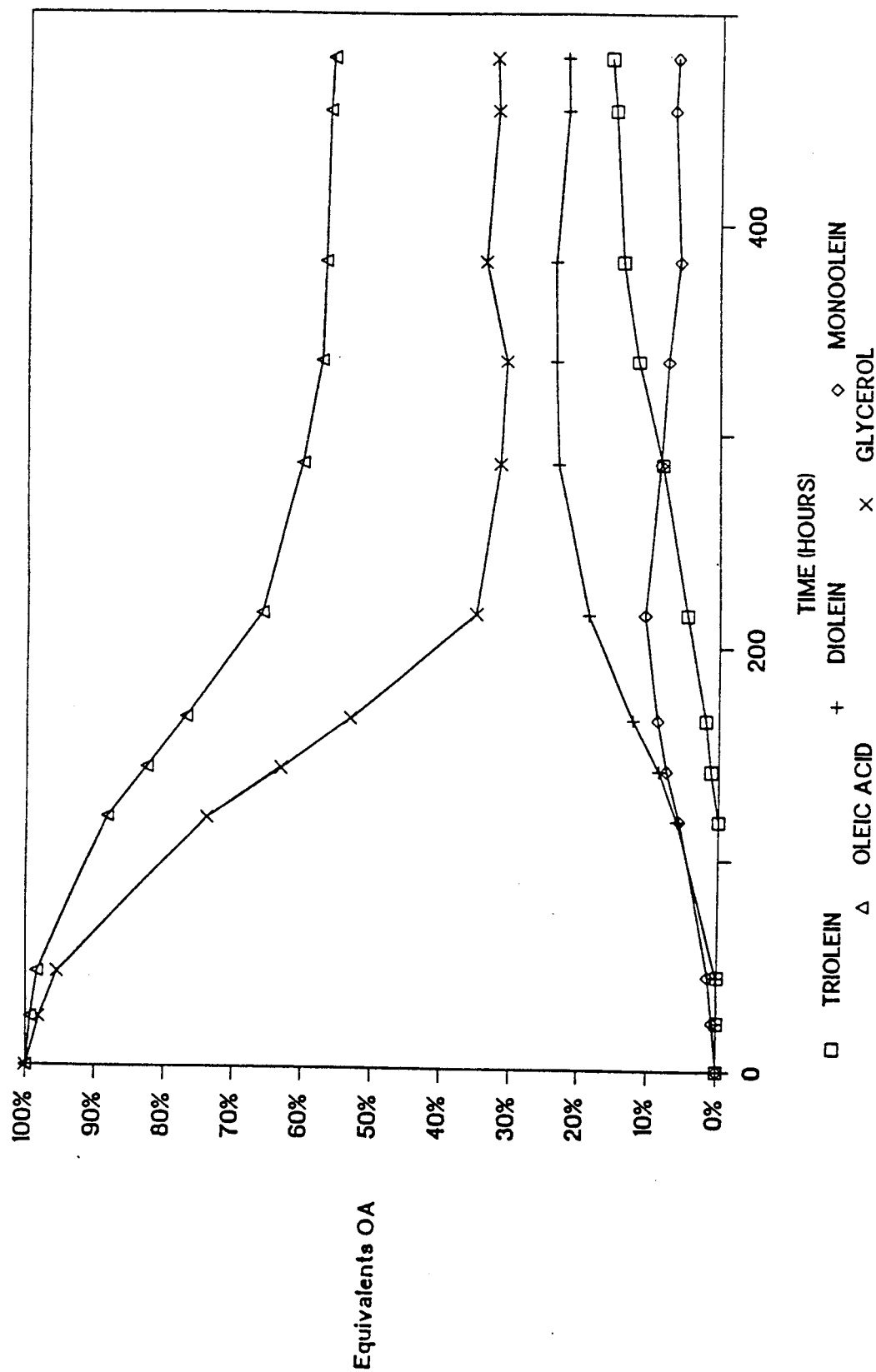
FIG. 18 represents the consumption of oleic acid through its enzymatic reaction with lipase and glycerol and the corresponding appearance of reaction products when concentrated lipase obtained from *Candida cylindracea* and immobilized using glutaraldehyde at a concentration of 0.75% is used.

The procedure described in Example 10 was repeated using the support of Example 7 as the source of lipase. Results are shown in FIG. 18.

EXAMPLE 17

Figure 19:
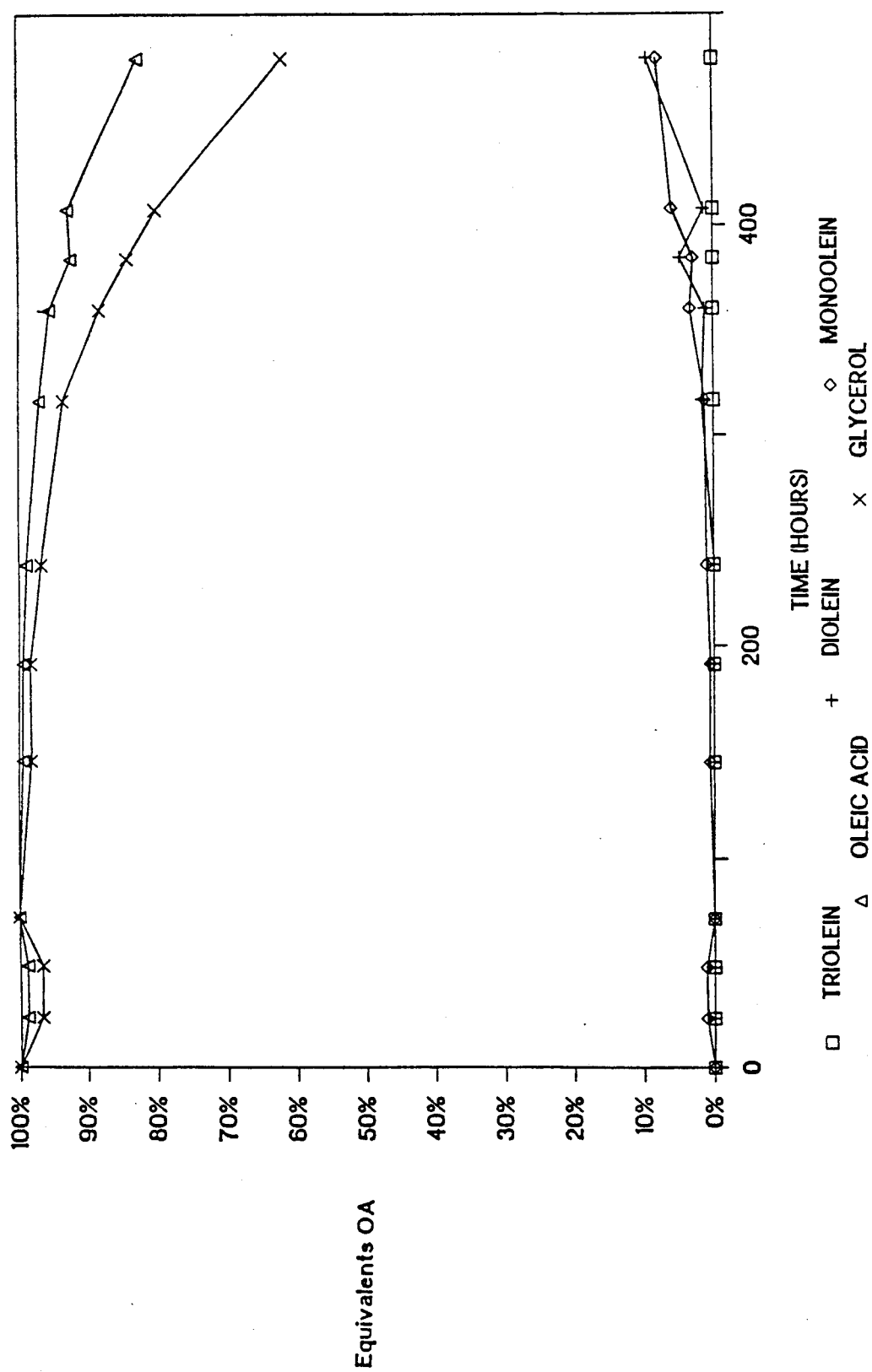
FIG. 19 represents the consumption of oleic acid through its enzymatic reaction with lipase and glycerol and the corresponding appearance of reaction products when concentrated lipase obtained from *Candida cylindracea* and immobilized using glutaraldehyde at a concentration of 1.5% is used.

The procedure described in Example 10 was repeated using the support of Example 8 as the source of lipase. Results are shown in FIG. 19.

EXAMPLE 18

The procedure described in Example 10 was repeated using the support of Example 5 as the source of lipase. FIGS. 7 to 11 represent the successive cycles of glycerides synthesis when reusing the same support.

EXAMPLE 19

Figure 12:
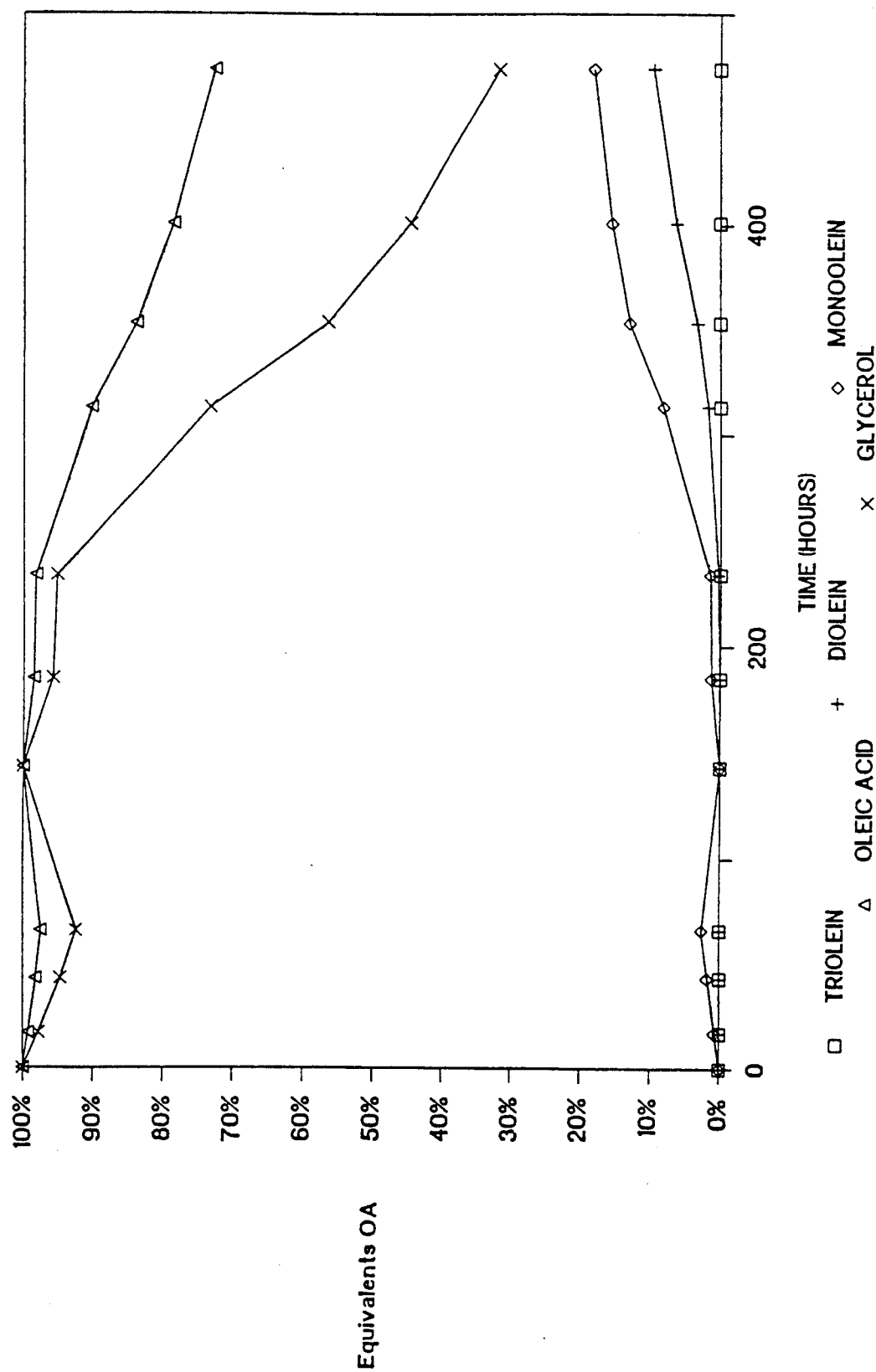
FIGS. 12 and 13 represent two successive cycles of consumption of oleic acid through its enzymatic reaction with lipase and glycerol and the corresponding appearance of reaction products when concentrated lipase obtained from *Candida cylindracea* and immobilized using glutaraldehyde at a concentration of 1.125% is used.
Figure 13:
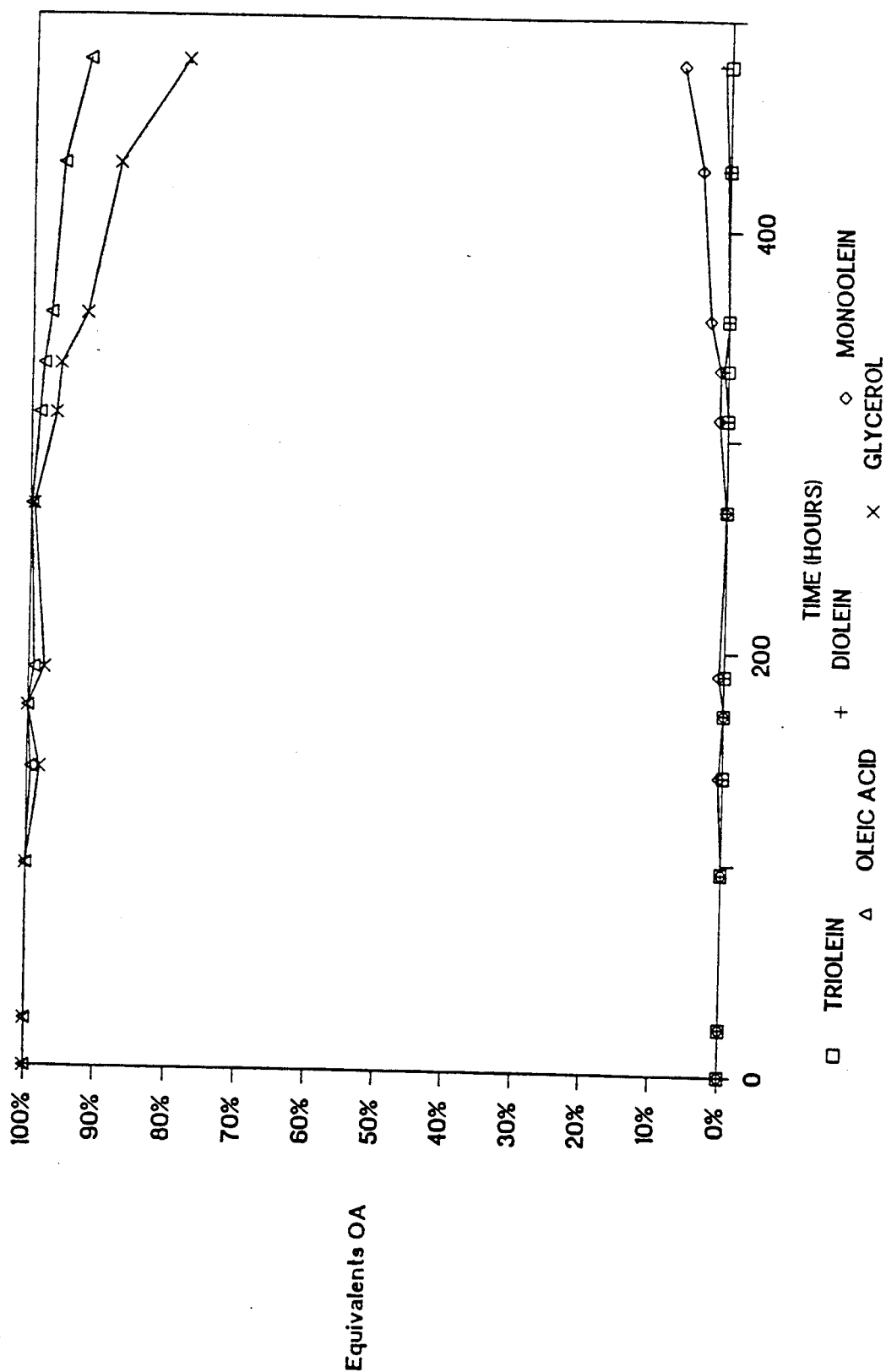

The procedure described in Example 10 was repeated using the support of Example 9 as the source of lipase. FIGS. 12 and 13 represent the successive cycles of glycerides synthesis when reusing the same support twice.

EXAMPLE 20

Figure 20:
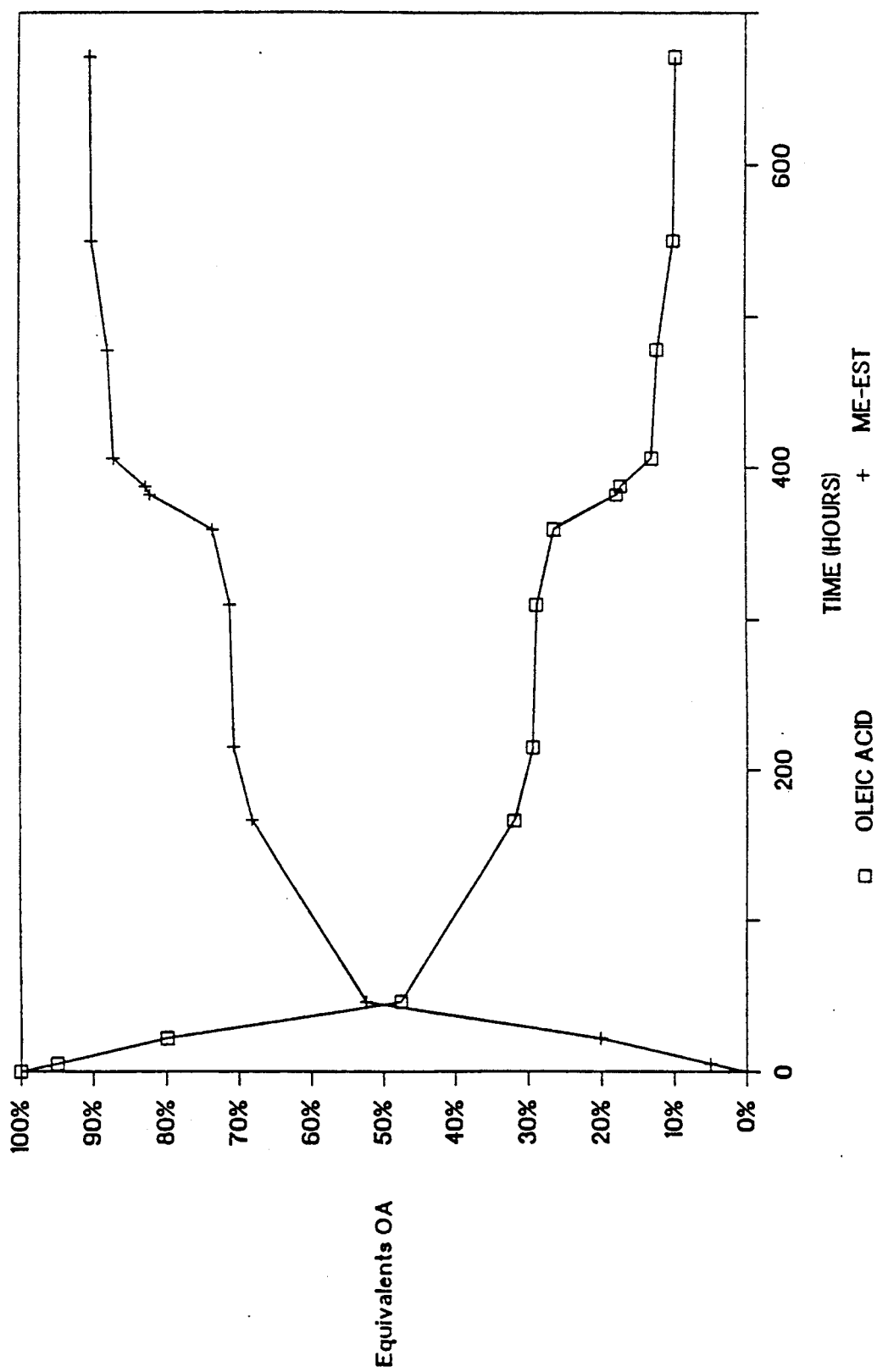
FIG. 20 represents the consumption of oleic acid through its enzymatic reaction with methanol and the corresponding appearance of reaction products when concentrated lipase obtained from *Rhizopus arrhizus* and immobilized using glutaraldehyde at a concentration of 1.125% is used.

Transformation of Oleic Acid and Methanol Into Oleic Acid Methyl Ester 0.5 g of oleic acid and 72 μl of methanol were reacted with the support prepared in Example 1 by strongly agitating the reaction mixture on an Eppendorf® mixer at 36° C. FIG. 20 represents the appearance of oleic acid methyl ester and the consumption of oleic acid. After 358 hours of reaction, 36 μl of methanol was added.

EXAMPLE 21

Figure 21:
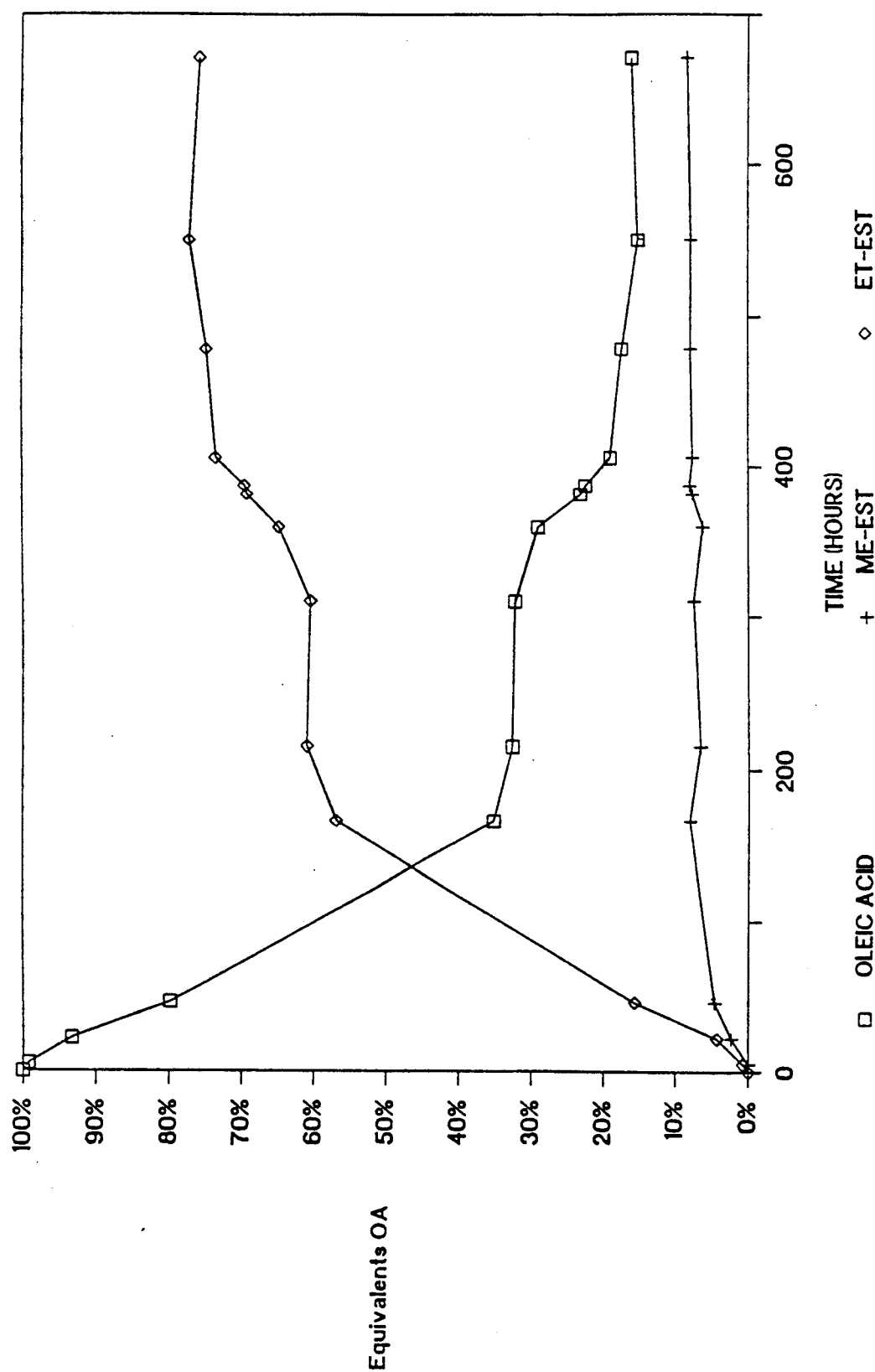
FIG. 21 represents the consumption of oleic acid through its enzymatic reaction with ethanol and the corresponding appearance of reaction products when concentrated lipase obtained from *Rhizopus arrhizus* and immobilized using glutaraldehyde at a concentration of 1.125% is used.

The procedure described in Example 21 was repeated using 103 μl of ethanol instead of methanol. FIG. 21 represents the appearance of oleic acid ethyl ester and the consumption of oleic acid. After 358 hours of reaction, 52 μl of ethanol was added.

What is claimed is:

1. A dry porous macromolecular matrix comprising a cross-linked mixture of 69.9 to 86.6% by weight of an inert protein and 0.4 to 10.2% by weight of a lipase enzyme and a cross-linking agent, the amount of cross-linking agent being about 11.7 to 23% by weight, said matrix being obtained by a process comprising:
    (i) adding to a buffer solution about 50 to 440 μl lipase enzyme, about 5% inert protein and about 0.75 to 1.5% bifunctional cross-linking agent and allowing the resultant mixture to react;
    (ii) freezing the resulting reacted mixture at a temperature ranging between −20° C. and −195° C.;
    (iii) allowing the frozen mixture to thaw to a temperature ranging from 4° to 25° C.; and
    (iv) rinsing and drying the resulting product at room temperature to produce said dry porous macromolecular matrix.

2. The matrix of claim 1, wherein the lipase enzyme originates from *Rhizopus arrhizus*, *Rhizopus delemar*, *Mucor miehei* or *Candida cylindracea*.

3. The matrix of claim 1, wherein the inert protein is bovine albumin.

4. The dry porous macromolecular matrix of claim 1, wherein the cross-linking agent is a bifunctional cross-linking agent.

5. The dry porous macromolecular matrix of claim 4, wherein the bifunctional cross-linking agent is glutaraldehyde.

6. The dry porous macromolecular matrix of claim 1, wherein the lipase enzyme originates from *Rhizopus arrhizus*, *Rhizopus delemar*, *Mucor miehei* or *Candida cylindracea*, the inert protein is bovine albumin and the cross-linking agent is glutaraldehyde.

7. The dry porous macromolecular matrix of claim 6, wherein the lipase enzyme originates from *Rhizopus arrhizus* and wherein the albumin concentration is 81.3% and the glutaraldehyde concentration is 18.3%.

8. The dry porous macromolecular matrix of claim 6, wherein the lipase enzyme originates from *Rhizopus arrhizus* and wherein the albumin concentration is 86.6% and the glutaraldehyde concentration is 13%.

9. The dry porous macromolecular matrix of claim 6, wherein the lipase enzyme originates from *Rhizopus arrhizus* and wherein the albumin concentration is 76.6% and the glutaraldehyde concentration is 23%.

10. The dry porous macromolecular matrix of claim 6, wherein the lipase enzyme originates from *Rhizopus delemar* and wherein the albumin concentration is 78.1% and the glutaraldehyde concentration is 11.7%.

11. The dry porous macromolecular matrix of claim 6, wherein the lipase enzyme originates from *Rhizopus delemar* and wherein the albumin concentration is 73.8% and the glutaraldehyde concentration is 16.6%.

12. The dry porous macromolecular matrix of claim 6, wherein the lipase enzyme originates from *Rhizopus delemar* and wherein the albumin concentration is 69.9% and the glutaraldehyde concentration is 21%.

13. The dry porous macromolecular matrix of claim 6, wherein the lipase enzyme originates from *Candida cylindracea* and wherein the albumin concentration is 84.5% and the glutaraldehyde concentration is 12.7%.

14. The dry porous macromolecular matrix of claim 6, wherein the lipase enzyme originates from *Candida cylindracea* and wherein the albumin concentration is 79.5% and the glutaraldehyde concentration is 17.9%.

15. The dry porous macromolecular matrix of claim 6, wherein the lipase enzyme originates from *Candida*

*cylindracea* and wherein the albumin concentration is 75% and the glutaraldehyde concentration is 22.5%.

16. A process for preparing a dry porous macromolecular matrix comprising a cross-linked mixture of 69.9 to 86.6% by weight of an inert protein, 0.4% to 10.2% by weight of a lipase enzyme and a bifunctional crosslinking agent, the amount of crosslinking agent being from about 11.7 to 23% by weight, said process comprising:

(i) adding to a buffer solution about 50 to 440 µl lipase enzyme, about 5% inert protein and about 0.75 to 1.5% bifunctional crosslinking agent and allowing the resultant mixture to react;

(ii) freezing the resulting reacted mixture at a temperature ranging between −20° C. and −195° C.;

(iii) allowing the frozen mixture to thaw to a temperature ranging from 4° to 25° C.; and (iv) rinsing and drying the resulting product at room temperature to produce said dry porous macromolecular matrix.

* * * * *

UNITED STATES PATENT AND TRADEMARK OFFICE
CERTIFICATE OF CORRECTION

PATENT NO. : 5,010,006
DATED : April 23, 1991
INVENTOR(S) : ERGAN et al

It is certified that error appears in the above-indentified patent and that said Letters Patent is hereby corrected as shown below:

On the title page, Item [54] and Column 1, line 1, change the title from "LIPASE IMMIOLIZED BY CROSS-LINKING WITH INERT PROTEIN FOR GLYCERIDE SYNTHESIS" to --LIPASE IMMOBILIZED BY CROSS-LINKING WITH INERT PROTEIN FOR GLYCERIDE SYNTHESIS--.

Signed and Sealed this

Twenty-fourth Day of August, 1993

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,010,006
DATED : April 23, 1991
INVENTOR(S) : ERGAN et al

It is certified that error appears in the above-identified patent and that said Letters Patent is hereby corrected as shown below:

Title page, Item [54], change the title from "LIPASE IMMDIOLIZED BY CROSS-LINKING WITH INERT PROTEIN FOR GLYCERIDE SYNTHESIS" to --LIPASE IMMOBILIZED BY CROSS-LINKING WITH INERT PROTEIN FOR GLYCERIDE SYNTHESIS--;

Title page, Item [75], the third named inventors first and last name, change "Gerald Andre" to --Gérald André--.

Signed and Sealed this

Ninth Day of November, 1993

Attest:

BRUCE LEHMAN

*Attesting Officer*  *Commissioner of Patents and Trademarks*